US00PP27609P2

(12) United States Plant Patent
Endisch

(10) Patent No.: US PP27,609 P2
(45) Date of Patent: Jan. 24, 2017

(54) ***PELARGONIUM* PLANT NAMED 'GENLICAL'**

(50) Latin Name: ***Pelargonium zonale*×*Pelargonium peltatum***
Varietal Denomination: Genlical

(71) Applicant: Gerd Endisch, Hagenbach (DE)

(72) Inventor: Gerd Endisch, Hagenbach (DE)

(73) Assignee: Endisch Gartenbau GMBH & Co. KG, Hagenbach (DE)

( * ) Notice: Subject to any disclaimer, the term of this patent is extended or adjusted under 35 U.S.C. 154(b) by 0 days.

(21) Appl. No.: 14/756,677

(22) Filed: Sep. 29, 2015

(51) Int. Cl.
*A01H 5/02* (2006.01)

(52) U.S. Cl.
USPC ..... Plt./324

(58) Field of Classification Search
USPC ..... Plt./324, 329, 332
CPC ..... A01H 5/0277
See application file for complete search history.

*Primary Examiner* — Kent L Bell

(57) ABSTRACT

A new and distinct cultivar of *Pelargonium* plant named 'Genlical' that is characterized by semi-double purple flowers, medium green foliage and an early flower response.

1 Drawing Sheet

Botanical classification: *Pelargonium zonale*×*Pelargonium peltatum.*

Variety denomination: 'Genlical'.

BACKGROUND OF THE INVENTION

The present invention relates to a new and distinct cultivar of *Pelargonium* plant botanically known as *Pelargonium zonale*×*Pelargonium peltatum* and hereinafter referred to by the cultivar name 'Genlical'.

The new cultivar is the product of a breeding program conducted by the inventor in a cultivated area of Hagenbach, Germany. The objective of the breeding program is to develop new *Pelargonium* cultivars that are early flowering with semi-double flowers and medium green foliage.

'Genlical' is a hybrid that originated from the induced hybridization of the female or seed parent a proprietary *Pelargonium zonale* identified by number W78 (not patented) and the male or pollen parent a proprietary *Pelargonium peltatum* identified by number U221 (not patented). The cultivar 'Genlical' was selected by the inventor in 2012 as a single plant within the progeny of the stated cross in a controlled environment of Hagenbach, Germany.

Asexual reproduction by terminal cuttings of the new cultivar 'Genlical' was first performed in 2012 in Hagenbach, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Pelargonium* cultivar 'Genlical'. These traits in combination distinguish 'Genlical' as a new and distinct cultivar apart from other known existing varieties of Geranium.

1. *Pelargonium* 'Genlical' exhibits purple flowers.
2. *Pelargonium* 'Genlical' exhibits semi-double flowers.
3. *Pelargonium* 'Genlical' exhibits medium green foliage without a zonation pattern.

4. *Pelargonium* 'Genlical' exhibits an early flower response.
5. *Pelargonium* 'Genlical' exhibits a moderate growth habit.

The closest comparison variety is *Pelargonium* 'PEQZ0002' (U.S. Plant Pat. No. 23,404). 'Genlical' is different than 'PEQZ0002' in having shorter internodes, foliage that is lighter green in color and flowers that are darker purple in color.

The new cultivar 'Genlical' is distinguishable from the female parent *Pelargonium* indentified as W78 in having foliage without a zonation pattern and flowers that are purple in color. The flowers of W78 are red.

The new cultivar 'Genlical' is distinguishable from the male parent *Pelargonium* identified as U221 in having flowers that are purple in color. The flowers of U221 are red-purple in color.

BRIEF DESCRIPTION OF THE DRAWING

The accompanying photograph illustrates the distinguishing traits of *Pelargonium* 'Genlical'. The plant in the photograph shows an overall view of a 12 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Pelargonium* cultivar named 'Genlical'. Data was collected in Hagenbach, Germany from 12 week old plants grown under glass greenhouse conditions. The plants were grown in 12 cm. diameter containers. The time of year was Spring and the daytime temperature ranged from 18 to 26° Centigrade. The temperature at night ranged from 16 to 20° Centigrade. The light level was 20 to 35 klux. No photoperiodic treatments were used. The growth retardant CYCOCEL 720 was applied at a rate of 0.05 percent. Color determinations are in accordance with The Royal Horticultural Society Colour Chart 2001 edition, except where general color terms of ordinary dictionary significance are used. The growing requirements are similar to the species.

'Genlical' has not been tested under all possible conditions and phenotypic differences may be observed with variations in environmental, climatic, and cultural conditions, however, without any variance in genotype.

Botanical classification: *Pelargonium zonale*×*Pelargonium peltatum* 'Genlical'.

Annual or perennial: Annual.

Parentage: 'Genlical' originated from the crossing of the female or seed parent a proprietary *Pelargonium zonale* identified by number W78 and the male or pollen parent a proprietary *Pelargonium peltatum* identified by number U221.

Vigor: Moderate.

Suitable container size: 11 to 14 cm. containers.

Growth rate: Approximately 6 cm. per month.

Growth habit: Upright, outwardly spreading.

Plant shape: Globose.

Plant height: Average 22 cm. in height.

Plant width: Average 24 cm. in width.

Propagation: Terminal cuttings.

Time to initiate roots: Approximately 5-7 days to produce roots at 20 degrees Centigrade.

Time to produce a rooted cutting or liner: Approximately 20-24 days at 20 degrees Centigrade.

Crop time: From an unrooted cutting, approximately 12 weeks.

High temperature tolerance: 40 degrees Centigrade.

Low temperature tolerance: 0 degrees Centigrade.

Root system: Fine and fibrous.

Stem:

*Branching habit.*—Free branching.
*Basal branching.*—Yes.
*Average number of lateral branches.*—5.
*Pinching.*—No.
*Lateral branch dimensions.*—12 to 17 cm. in length and 6 to 8 mm. in diameter.
*Internode length.*—1.5 to 4.0 cm. between nodes.
*Lateral branch strength.*—Moderate.
*Color.*—143B.
*Pubescence.*—Present.
*Shape.*—Round.
*Surface.*—Glabrous, slightly glossy.

Foliage:

*Leaf arrangement.*—Alternate.
*Compound or single.*—Single.
*Quantity of leaves per lateral branch.*—Average 14.
*Leaf shape.*—Reniform.
*Leaf apex.*—Rounded.
*Leaf base.*—Cordate.
*Leaf length.*—5.5 to 7.0 cm. in length.
*Leaf width.*—8.0 to 9.5 cm. in width.
*Pubescence.*—Present both sides.
*Leaf margin.*—Bicrenate, slightly wavy.
*Texture.*—Both sides smooth.
*Vein pattern.*—Pinnate.
*Young leaf color* (*upper surface*).—146B.
*Young leaf color* (*lower surface*).—137C to 137D.
*Mature leaf color* (*upper surface*).—137B.
*Mature leaf color* (*lower surface*).—137C.
*Vein color* (*upper surface*).—137C.
*Vein color* (*lower surface*).—146C.
*Zonation.*—Absent.
*Leaf attachment.*—Petiolate.
*Petiole dimensions.*—5 to 8 cm. in length and 2 to 2.5 mm. in diameter.
*Petiole color.*—137B.

Stipules:

*Stipule dimensions.*—0.8 cm. in length and 1.2 cm. in width.
*Stipule color.*—143C.

Inflorescence:

*Inflorescence arrangement.*—Rounded hemispherical umbels.
*Inflorescence type.*—Umbel.
*Inflorescence dimensions.*—7.5 cm. in height and 12.8 cm. in width.
*Flowering habit.*—Continuous.
*Quantity of flowers and buds per inflorescence.*—Approximately 25 to 35.
*Quantity of open flowers per lateral branch.*—Approximately 6.
*Flowering season.*—Spring to Summer.
*Time to flower.*—Approximately 11 weeks.
*Fragrance.*—None.
*Bud dimensions.*—9 mm. in length and 5.5 mm. in diameter.
*Bud shape.*—Ovoid.
*Bud color.*—143B.
*Rate of bud opening.*—3 days.
*Flower aspect.*—Upright.
*Flower shape.*—Initially cup-shaped then flattening to shallow cup-shaped, rounded, semi-double.
*Flower dimensions.*—5.0 to 5.4 cm. in diameter and 1.7 to 1.9 cm. in depth.
*Flower longevity.*—Lasts approximately 10 days on plant.
*Self-cleaning or persistent.*—Persistent.
*Petal texture.*—Glabrous both sides.
*Petal arrangement.*—Zygomorph.
*Number of petals.*—6 to 7 in number.
*Petal shape.*—Ovate.
*Petal margin.*—Entire.
*Petal apex.*—Rounded.
*Petal base.*—Attenuate.
*Petal dimensions.*—2.6 cm. in length and 2.1 cm. in width.
*Upper petal color fully opened* (*upper side*).—78A.
*Lower petal color fully opened* (*upper side*).—78A.
*Upper petal color fully opened* (*under side*).—78B to 78C.
*Lower petal color fully opened* (*under side*).—78B to 78C.
*Petaloid arrangement.*—Irregular.
*Number of petaloids.*—2 to 4.
*Petaloid shape.*—Sail shaped.
*Petaloid margin.*—Entire.
*Petaloid dimensions.*—1 cm. in length and 2 mm. in width.
*Petaloid color.*—78A.

Sepals:

*Number of sepals.*—5.
*Sepal surface.*—Upper side: dull and pubescent, Lower side: smooth.
*Sepal shape.*—Lanceolate.
*Sepal margin.*—Entire.
*Sepal apex.*—Acute.
*Sepal base.*—Cuneate.

*Sepal dimensions.*—1.0 cm. in length and 3 mm. in width.
*Sepal color mature* (*upper side*).—143B, base 41A.
*Sepal color mature* (*under side*).—143B, base 41A.
*Calyx shape*.—Cup-shaped.
*Calyx dimensions.*—9 mm. in length, 1.7 cm. in diameter and 6 mm. in height.

Peduncle:
*Peduncle dimensions.*—12 cm. in length and 3 mm. in diameter.
*Peduncle angle.*—10° from vertical.
*Peduncle color.*—147B.
*Peduncle strength*.—Moderately strong.

Pedicels:
*Pedicel dimensions.*—2 cm. in length and 1.2 mm. in diameter.
*Pedicel angle.*—45°.
*Pedicel color.*—178A to 178B.
*Pedicel strength*.—Moderate.

Reproduction organs:
*Stamen number.*—5 to 7.
*Anther shape*.—Ovate.
*Anther dimensions.*—2.5 mm in length.
*Anther color.*—61B.
*Amount of pollen*.—Moderate.
*Pollen color.*—31A.
*Pistil number.*—1 in number.
*Pistil dimensions.*—8 mm. in length.
*Stigma shape*.—Five parted, star shaped.
*Stigma color.*—46A.
*Style length.*—5 mm.
*Style color.*—46A.
*Ovary color.*—143B.

Fruit and seed: Fruit and seed production has not been observed to date.

Disease and pest resistance: Plants of the new *Pelargonium* have not been observed for disease or pest resistance to date.

It is claimed:

1. A new and distinct variety of *Pelargonium* plant named 'Genlical' as described and illustrated.

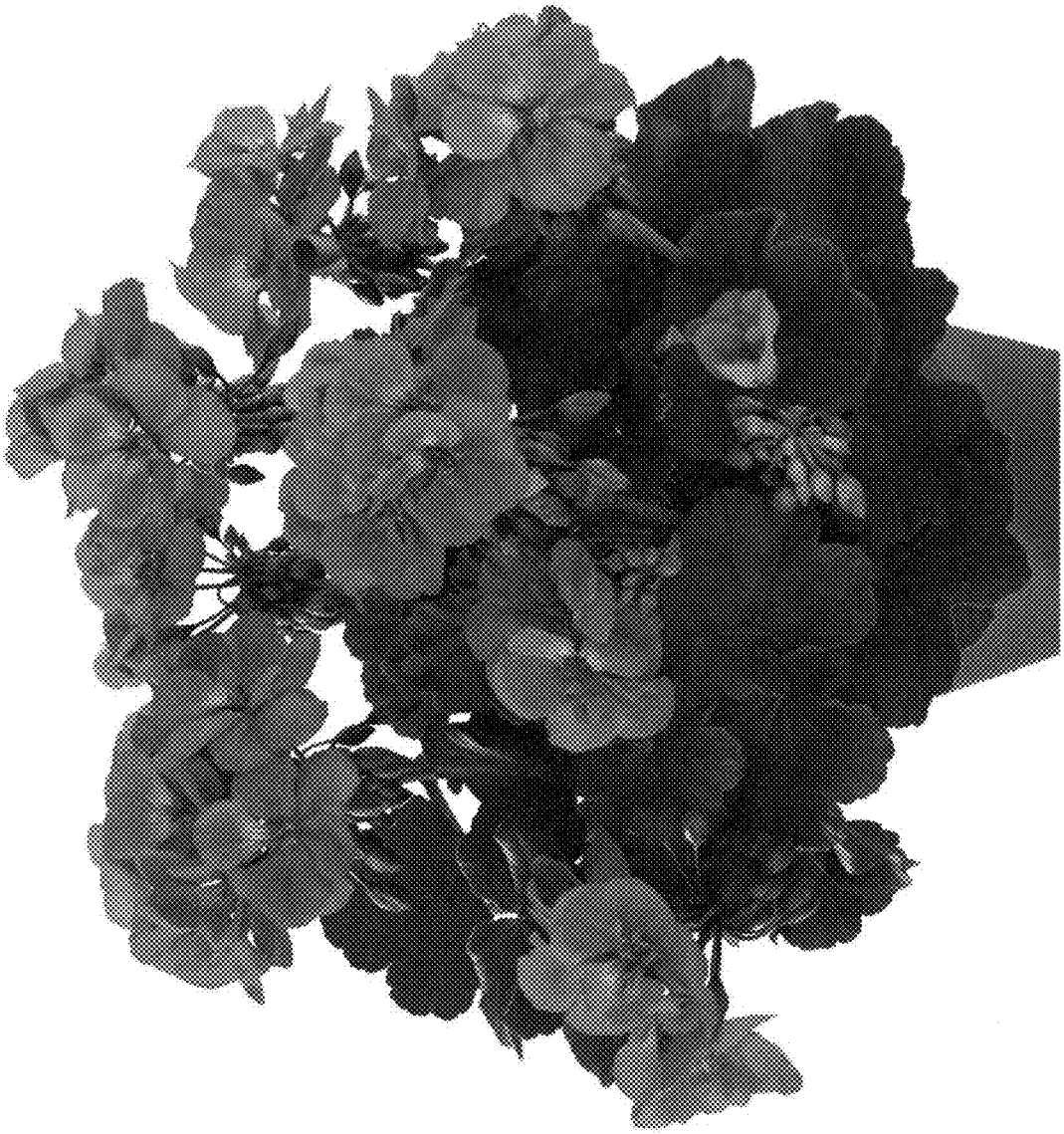

* * * * *